(12) United States Patent
Zimmermann et al.

(10) Patent No.: US 10,199,985 B2
(45) Date of Patent: Feb. 5, 2019

(54) TECHNIQUE FOR DETECTING A DEFECT IN A MULTI-JUNCTION SOLAR CELL

(71) Applicant: Airbus DS GmbH, Taufkirchen (DE)

(72) Inventors: Claus Zimmermann, Munich (DE); Helmut Nesswetter, Isen (DE); Martin Rutzinger, Munich (DE)

(73) Assignee: AIRBUS DS GMBH, Taufkirchen (DE)

( * ) Notice: Subject to any disclaimer, the term of this patent is extended or adjusted under 35 U.S.C. 154(b) by 8 days.

(21) Appl. No.: 15/434,152

(22) Filed: Feb. 16, 2017

(65) Prior Publication Data

US 2017/0237396 A1      Aug. 17, 2017

(30) Foreign Application Priority Data

Feb. 16, 2016      (EP) ..................... 16155895

(51) Int. Cl.

| | |
|---|---|
| *H02S 50/15* | (2014.01) |
| *G01N 21/64* | (2006.01) |
| *G01N 21/88* | (2006.01) |
| *G06T 7/00* | (2017.01) |
| *G06T 11/60* | (2006.01) |
| *H01L 31/06* | (2012.01) |

(52) U.S. Cl.
CPC ......... *H02S 50/15* (2014.12); *G01N 21/6489* (2013.01); *G01N 21/8806* (2013.01); *G06T 7/0004* (2013.01); *G06T 11/60* (2013.01); *H01L 31/06* (2013.01)

(58) Field of Classification Search
CPC ..... H02S 50/15; H01L 31/06; G01N 21/6489; G01N 21/8806; G06T 7/0004; G06T 11/60

See application file for complete search history.

(56) References Cited

U.S. PATENT DOCUMENTS

2010/0271633 A1* 10/2010 Gomi ................. G01N 21/6489
356/448
2011/0255772 A1   10/2011 Zimmermann

OTHER PUBLICATIONS

European Search Report, dated May 25, 2016, priority document.
"Electroluminescence and photoluminescence characterization of multijunction solar cells" Newsswetter et al., Jun. 3, 2012.

* cited by examiner

*Primary Examiner* — Ruiping Li
(74) *Attorney, Agent, or Firm* — Greer, Burns & Crain, Ltd.

(57) ABSTRACT

A method for detecting a defect in a multi-junction solar cell is presented. The multi-junction solar cell comprises at least two vertically stacked p-n junctions. The method comprises exciting a first p-n junction of the at least two vertically stacked p-n junctions by illuminating the solar cell with excitation light in a first excitation wavelength range, detecting photoluminescence light emitted by photoluminescence of the first p-n junction, and generating a spatially resolved first photoluminescence image of the photoluminescence light emitted by the first p-n junction. Further, a computer program product and an apparatus for detecting a defect in a multi-junction solar cell are presented.

14 Claims, 13 Drawing Sheets

TECHNIQUE FOR DETECTING A DEFECT IN A MULTI-JUNCTION SOLAR CELL

CROSS-REFERENCES TO RELATED APPLICATIONS

This application claims the benefit of the European patent application No. 16155895.2 filed on Feb. 16, 2017, the entire disclosures of which are incorporated herein by way of reference.

TECHNICAL FIELD

The present disclosure relates to a technique for detecting a defect in a multi-junction solar cell. The technique may be embodied in at least one method and/or at least one apparatus.

BACKGROUND OF THE INVENTION

Virtually all spacecraft today are solar powered. The solar cells used are typically triple junction solar cells based on III-V semiconductor with an efficiency of 30% under the AM0 spectrum in space. These cells are mounted on rigid carbon fiber/Al honeycomb core sandwich panels with the help of silicone adhesives. During operation in space, these solar panels are exposed to severe temperature variations, ranging from −180° C. to +100° C., for example, during an eclipse phase in a geostationary orbit. Since the thermal expansion coefficient of the structure is virtually zero, in contrast to the non-negligible expansion coefficient of the cell, severe thermal stresses are induced in the cell. While the solar panel design can be tailored in such a way that the integrity of the cells is ensured even under these thermal stresses, this is not the case if pre-existing mechanical defects are present. The externally applied stresses are concentrated at the tip of a cell crack which results in crack growth. This can result in power loss in orbit. For this reason, it is of vital importance to detect and document mechanical cell defects on a solar panel accurately.

The de-facto industry standard is a cell inspection with the help of electroluminescence. By forward biasing the entire cell, each junction emits a characteristic electroluminescence, which can be recorded by appropriate cameras. Mechanical cell defects can be clearly identified in the image. While this method is fairly reliable in detecting mechanical defects, a drawback is that each cell has to be contacted electrically, making this method quite complex to implement on an actual solar array panel. There, several cells are connected in series to form a string. Several strings are then connected in parallel. Typically, each string has to be contacted individually to a power source. In an automated inspection flow, the image acquisition camera moves along a certain path and each string is forward biased depending on the camera position on the panel. Therefore, next to the electrical contacting effort, the entire electrical layout with the start and end point of each string has to be programmed first. Another drawback of the electroluminescence inspection is that it can only be performed on fully processed cells, but not on earlier stages in the cell production.

SUMMARY OF THE INVENTION

It is therefore an object of the present disclosure to provide a technique for detecting defects in solar cells, which avoids one or more of the drawbacks discussed above, or other related problems.

According to a first aspect, a method for detecting a defect in a multi-junction solar cell comprising at least two vertically stacked p-n junctions is provided. The method comprises exciting a first p-n junction of the at least two vertically stacked p-n junctions by illuminating the solar cell with excitation light in a first excitation wavelength range, detecting photoluminescence light emitted by photoluminescence of the first p-n junction, and generating a spatially resolved first photoluminescence image of the photoluminescence light emitted by the first p-n junction.

Although in the following, details with regard to the first aspect are discussed, these details also hold for the other aspects described in this disclosure, where applicable.

In this disclosure, the expressions "first," "second," "third," etc., are provided merely for distinguishing between different elements and/or entities. These expressions are not limiting with regard to an arrangement or any other properties of the respective element or entity. For example, the expression "first p-n junction" is merely used to enable distinction from a "second p-n junction" and a "third p-n junction", and so forth. The expression "first p-n junction" does not imply any properties of this p-n junction, such as an arrangement within the solar cell or a bandgap energy.

The p-n junctions may be "vertically stacked" in the following sense. Each p-n junction may represent a boundary between a p-type layer and an n-type layer of a semiconductor material. The order of the p and n type layers can also be reversed in n on p type junctions. The expression "p-n junction" according to this disclosure also encompasses p-i-n junctions comprising an intrinsic layer between the p-type layer and the n-type layer of the p-n junction. For example, such a p-i-n junction may comprise a p-i-n structure consisting of a thick intrinsic (i) layer for the photon absorption and thin, highly doped p- and n-type layers at the front/rear side to form a drift solar cell. The p-type layer and the n-type layer of each p-n junction may extend within a horizontal plane, wherein a vertical direction is defined along a normal direction of this horizontal plane. The p-n junctions may be stacked on top of each other along this vertical direction.

The multi-junction solar cell may comprise two or more p-n junctions, wherein a topmost p-n junction may be provided at a light incidence surface side of the solar cell. The p-n junctions may be provided in the solar cell, such that the topmost p-n junction has the largest bandgap energy and the bandgap energies of the p-n junctions decrease towards the lower p-n junctions.

Exciting the first p-n junction may be carried out by providing excitation light within a narrow wavelength band (i.e., the first excitation wavelength range). For this, a narrow wavelength band light source may be provided, such as an LED or a laser. Additionally or alternatively, at least one suitable optical filter may be used for providing light with in the first excitation wavelength range. For example, at least one of a longpass filter, a shortpass filter, and a bandpass filter may be used to provide the excitation light in the first excitation wavelength range. The first excitation wavelength range may comprise a wavelength component suitable for exciting the first p-n junction. For example, the first excitation wavelength range may have a center wavelength which is smaller than a wavelength corresponding to the bandgap energy of the first p-n junction. In this disclosure, the expression "center wavelength" may represent a wavelength of a particular wavelength band, which has the highest intensity in the wavelength band.

For detecting the photoluminescence light, suitable optical elements, such as lenses may be provided. Further, the photoluminescence light may be separated from the excitation light by using suitable filters. For example, at least one of a longpass filter, a shortpass filter, a bandpass filter, and a notch filter may be used. The at least one filter may be provided such that only photoluminescence light may pass to a detector used for detecting the photoluminescence light. For example, a longpass filter may be provided for blocking the excitation light and for letting pass the longer-wavelength photoluminescence light emitted by the first p-n junction. Further, at least one suitable filter may be used for blocking photoluminescence light emitted from p-n junctions other than the first p-n junction.

The "first p-n junction" is not limited to, e.g., a topmost p-n junction in the solar cell and any of the at least two vertically stacked p-n junctions may be selected to be the first p-n junction (e.g., the p-n junction adjacent to the topmost p-n junction).

The spatially resolved first photoluminescence image of the photoluminescence light emitted by the first p-n junction may be, e.g., a two-dimensional image, showing a top view of the solar cell (along the vertical direction). Pixel values of this image may represent intensity values of the detected photoluminescence light. The image may be represented, e.g., by a black-and-white image or by a color-coded image. The image does not necessarily have to be displayed to a user. Generating the spatially resolved first photoluminescence image of the photoluminescence light emitted by the first p-n junction may comprise merely storing the image in the form of a file or in the form of a data set in a memory. The memory may be a volatile or non-volatile memory.

The method may further comprise exciting a second p-n junction of the at least two vertically stacked p-n junctions by illuminating the solar cell with excitation light in a second excitation wavelength range.

The above remarks concerning exciting the first p-n junction apply accordingly to exciting the second p-n junction. For example, a respective light source and/or at least one optical filter may be used for generating excitation light in the second excitation wavelength range. The second p-n junction may be a p-n junction adjacent to the first p-n junction. Further, the method is not limited to the illumination of two p-n junctions only, it may also further involve exciting a third p-n junction and/or more than three p-n junctions.

The method may further comprise observing the first image for spatial intensity variations.

The step of observing may be carried out visually by a person (a user) and/or may be carried out by a computer having a respective observation unit. Further, interim solutions, such as a computer-aided visual observation step may be implemented. The method may further comprise a judging step of judging whether a spatial intensity variation corresponds to a defect or not. The judging step may be carried out based on a shape of the intensity variation.

Observing the first image for spatial intensity variations may comprise observing the first image for exponential intensity variations.

For example, an observation unit may be provided which is configured to detect exponential intensity variations. The observation unit may be configured to differentiate between exponential intensity variations and other (e.g., linear) intensity variations. In case an exponential intensity variation is detected, this intensity variation may be judged to belong to a defect in the solar cell, such as a crack.

The method may further comprise exciting the first p-n junction of the at least two vertically stacked p-n junctions by illuminating the solar cell with excitation light in the first excitation wavelength range at a first illumination intensity that is constant over time, exciting the second p-n junction of the at least two vertically stacked p-n junctions by illuminating the solar cell with excitation light in the second excitation wavelength range at a second illumination intensity that changes over time, generating a plurality of photoluminescence images while the second illumination intensity is changed over time, and observing the generated plurality of photoluminescence images for regions in which the intensity changes over time.

Generating a plurality of photoluminescence images may include generating the first photoluminescence image and generating at least one further photoluminescence image after or before the first photoluminescence image is generated. The regions in which the intensity of the photoluminescence image changes over time may be attributed to a defect in the solar cell (e.g., a crack). For example, a predefined threshold value for change of intensity may be set for deciding whether a particular region of the solar cell is judged to exhibit a defect or not.

The method may further comprise generating the first photoluminescence image of photoluminescence light emitted by photoluminescence of the first p-n junction under excitation of the first p-n junction at a first illumination intensity and under excitation of the second p-n junction at a second illumination intensity, generating a second photoluminescence image of photoluminescence light emitted by photoluminescence of the first p-n junction under excitation of the first p-n junction at the first illumination intensity and under excitation of the second p-n junction at a third illumination intensity different from the second illumination intensity, combining the first photoluminescence image and the second photoluminescence image to a third photoluminescence image by using a mathematical operation, and observing the third photoluminescence image for spatial intensity variations.

For combining the first and the second photoluminescence image, a combining unit may be provided. The combining unit may comprise a computer for performing the combining step. Observing the third photoluminescence image for spatial intensity variations may be carried out by a user or automatically by an observing unit. The user and/or the observation unit may judge that a particular intensity variation corresponds to a defect in the solar cell. Further, the second p-n junction may be excited by an illumination intensity that changes over time. In this case, a plurality of third photoluminescence images may be generated, e.g., by combining the first photoluminescence image with further second photoluminescence images that have been generated from photoluminescence light emitted by photoluminescence of the first p-n junction under excitation of the first p-n junction at the first illumination intensity and under excitation of the second p-n junction at the illumination intensity that changes over time. In this case, the generated third illumination images may be observed for regions in which the intensity changes over time.

The mathematical operation may be a subtraction of intensity values of one of the first and second photoluminescence image from the other of the first and second photoluminescence image.

Exciting the first p-n junction of the at least two vertically stacked p-n junctions by illuminating the solar cell with excitation light in a first excitation wavelength range may be carried out at a first illumination intensity that is configured to create a photocurrent in the first p-n junction in a range of 1 to 100 mA/cm2, in particular in a range of 10 to 20 mA/cm2.

Exciting the second p-n junction of the at least two vertically stacked p-n junctions by illuminating the solar cell with excitation light in a second excitation wavelength range may be carried out at a second illumination intensity that is configured to create a photocurrent in the second p-n junction in a range of 1 to 100 mA/cm2, in particular in a range of 10 to 20 mA/cm2.

For measuring the illumination intensity in units of generated photocurrent in a particular p-n junction, a calibration measurement may be performed. In the calibration measurement, it may be determined, which illumination power value corresponds to which photocurrent value. In the following steps of the method, a measured illumination power value (e.g., by using a power meter) may be converted to a value of generated photocurrent by applying the information derived from the calibration measurement. Additionally or alternatively, a simulation may be used.

A center wavelength of the photoluminescence light emitted by photoluminescence of the first p-n junction may be not included in the first excitation wavelength range.

In other words, excitation of the first p-n junction of the at least two vertically stacked p-n junctions by illuminating the solar cell with excitation light in the first excitation wavelength range may be carried out such that a wavelength corresponding to the bandgap of the first p-n junction is not included in the first excitation wavelength range. For example, the first excitation wavelength range may comprise only wavelengths shorter than the center wavelength of the photoluminescence light emitted by photoluminescence of the first p-n junction.

A center wavelength of the photoluminescence light emitted by photoluminescence of the first p-n junction may be not included in the first excitation wavelength range. A center wavelength of the photoluminescence light emitted by photoluminescence of the first p-n junction may be not included in the second excitation wavelength range. The first excitation wavelength range and the second excitation wavelength range may be configured such that they do not overlap each other.

Excitation of the second p-n junction of the at least two vertically stacked p-n junctions by illuminating the solar cell with excitation light in the second excitation wavelength range may be carried out such that a wavelength corresponding to the bandgap of the first p-n junction is not included in the second excitation wavelength range. For example, the second excitation wavelength range may comprise only wavelengths shorter than the center wavelength of the photoluminescence light emitted by photoluminescence of the first p-n junction.

The first excitation wavelength range and the second excitation wavelength range may be configured such that independent excitation of the first p-n junction and the second p-n junction can be performed. For example, the second excitation wavelength range may be configured such that it does not comprise an excitation wavelength of the first p-n junction. Further, the first excitation wavelength range may be configured such that it does not comprise an excitation wavelength of the second p-n junction.

According to a second aspect, a computer program product stored on a computer-readable storage device is provided. The computer program product comprises program code portions for performing the steps of any of the methods described in this disclosure when the computer program product is executed on a computing device.

According to a third aspect, an apparatus for detecting a defect in a multi-junction solar cell comprising at least two vertically stacked p-n junctions is provided. The apparatus comprises a first illumination unit configured to excite a first p-n junction of the at least two vertically stacked p-n junctions by illuminating the solar cell with excitation light in a first excitation wavelength range, a detecting unit configured to detect photoluminescence light emitted by photoluminescence of the first p-n junction, and an image generating unit configured to generate a spatially resolved first photoluminescence image of the photoluminescence light emitted by the first p-n junction.

The apparatus may further comprise a second illumination unit configured to excite a second p-n junction of the at least two vertically stacked p-n junctions by illuminating the solar cell with excitation light in a second excitation wavelength range.

The image generating unit may be configured to generate the first photoluminescence image of photoluminescence light emitted by photoluminescence of the first p-n junction under excitation of the first p-n junction at a first illumination intensity and under excitation of the second p-n junction at a second illumination intensity and to generate a second photoluminescence image of photoluminescence light emitted by photoluminescence of the first p-n junction under excitation of the first p-n junction at the first illumination intensity and under excitation of the second p-n junction at a third illumination intensity different from the second illumination intensity. The apparatus may further comprise a combining unit configured to combine the first photoluminescence image and the second photoluminescence image to a third photoluminescence image by using a mathematical operation, and an observation unit configured to observe the third photoluminescence image for spatial intensity variations.

Even if some of the aspects described above have been described in relation to physical defects, such as cracks, in a multi-junction solar cell, these aspects can also be implemented for detecting other features in multi-junction solar cells, such as shunts caused by growth defects.

BRIEF DESCRIPTION OF THE DRAWINGS

Embodiments of the technique presented herein are described below with reference to the accompanying drawings, in which.

In the following, but without limitation thereto, specific details are expounded in order to give a full understanding of the present disclosure. It is clear to persons skilled in the art, however, that the present invention can be used in other embodiments, which can differ from the details expounded in the following.

DETAILED DESCRIPTION OF THE PREFERRED EMBODIMENTS

Figure 1:
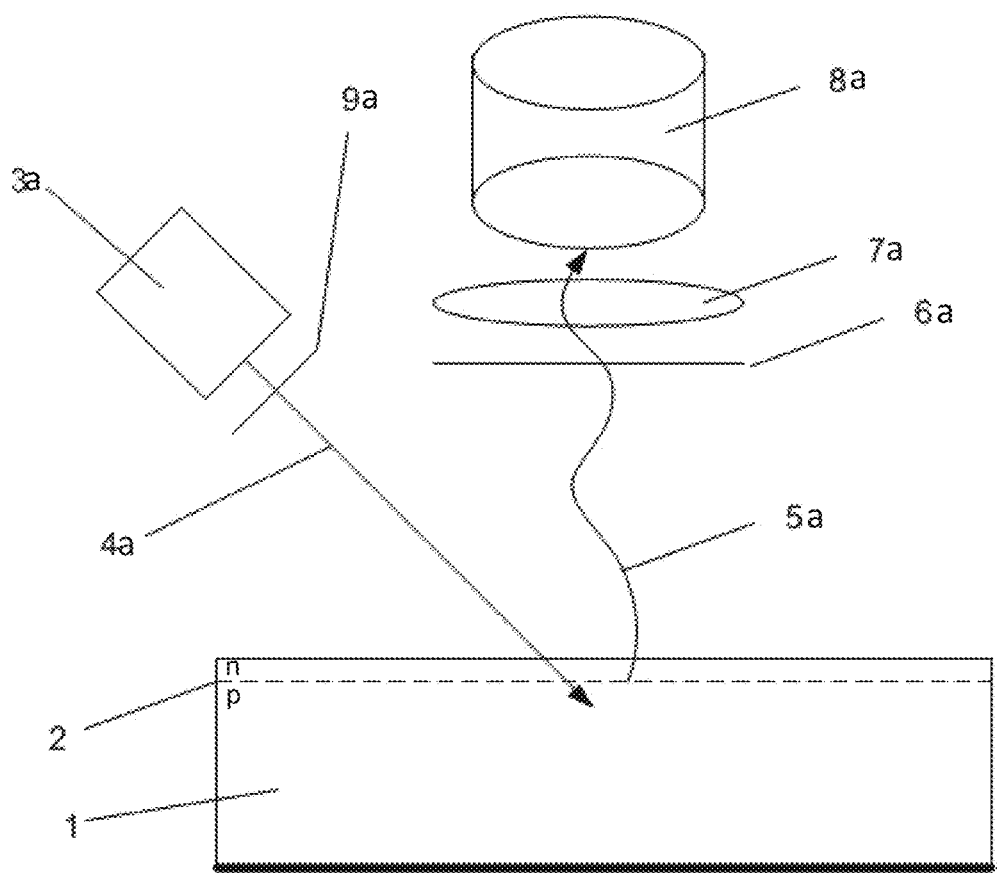
FIG. 1 shows a schematic representation of a photoluminescence setup for a single junction solar cell.

FIG. 1 shows a photoluminescence imaging setup for generating a photoluminescence image of a single junction solar cell. The setup is useful for understanding the underlying principles of the present disclosure. In the photoluminescence imaging setup according to FIG. 1, in contrast to electroluminescence where an external current generates electron-hole pairs that recombine radiatively, an external light source 3a is used to generate the charge carriers in the solar cell 1 consisting of one p-n junction 2. The charge carriers then also recombine radiatively and generate photoluminescence light 5a under open circuit conditions. By using appropriate filters 6a, 9a, the photoluminescence light 5a of the p-n junction 2 can be separated from an exciting radiation 4a and recorded by an appropriate detector 8a, like a CCD or CMOS camera spatially resolved, sometimes aided by additional optical elements like lenses 7a. The photoluminescence light 5a is emitted at a central wavelength corresponding to the bandgap energy of the semiconductor material used, with a narrow spread. Therefore, it is beneficial if the light source 3a also produces an illumination with a narrow distribution of wavelengths. The wavelength of the exciting radiation is preferably smaller than the wavelength of the photoluminescence 5a. This can be achieved by using narrow wavelength band light sources like light emitting diodes (LEDs) or lasers, or combining a light source 3a with a filter 9a. The filter 6a of the detection system only needs to block all exciting radiation, e.g. reflected from the surface, in order to isolate the photoluminescence 5a of the cell 1.

Figure 2:
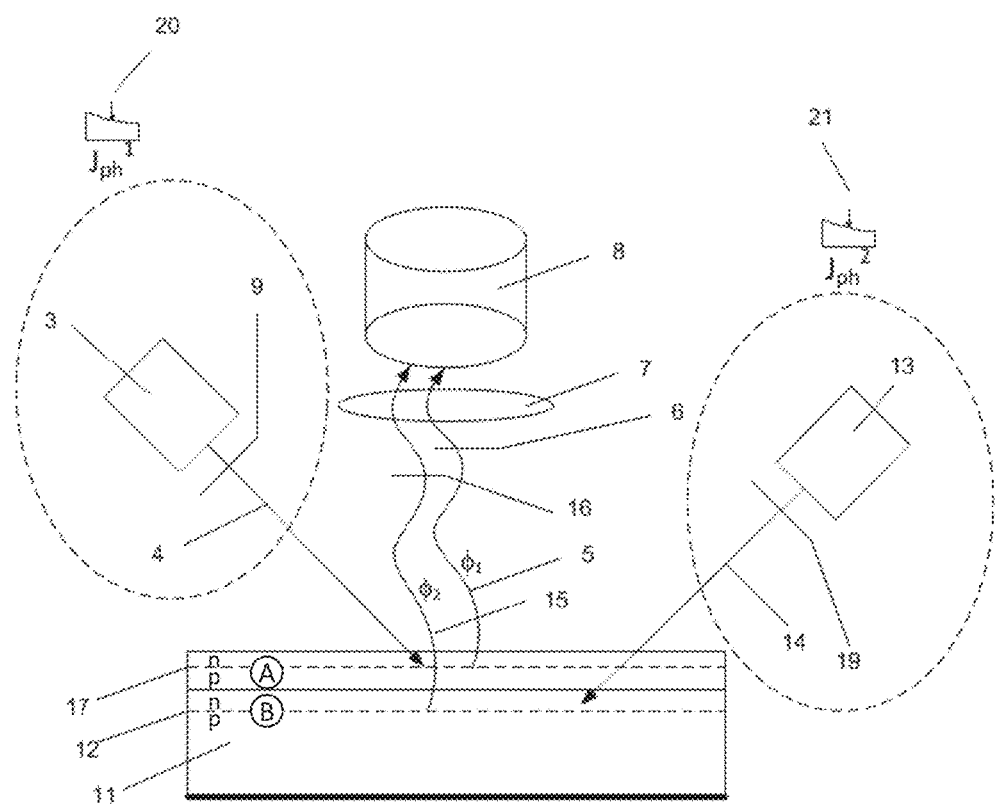
FIG. 2 shows a schematic representation of a photoluminescence setup for a dual junction solar cell.

FIG. 2 shows a photoluminescence imaging setup for generating a photoluminescence image of a dual junction solar cell. The setup of FIG. 2 may be used, e.g., for carrying out a method for detecting a defect in a multi-junction solar cell as described below with reference to FIGS. 10 to 12. For multi-junction cells 11, containing at least two p-n junctions A 17 and B 12 stacked on top of each other as shown in FIG. 2, photoluminescence imaging has an additional advantage. By using two different illumination units 3, 9 and 13, 19 each of which produces radiation 4, 14 predominantly absorbed in one p-n junction only, the photocurrents $J_{ph}^1$ 20 and $J_{ph}^2$ 21 in the p-n junctions 12, 17 can be adjusted independently. By using different filter elements 6, 16 the photoluminescence $\Phi 1$ 5 of junction A or $\Phi 2$ 15 of junction B can be recorded spatially resolved by the detection system 7, 8. The possibility to adjust the photocurrent in each p-n junction 12, 17 independently enables an adjustment of the contrast of mechanical (and also electrical) defects as shown in the following.

Figure 3:
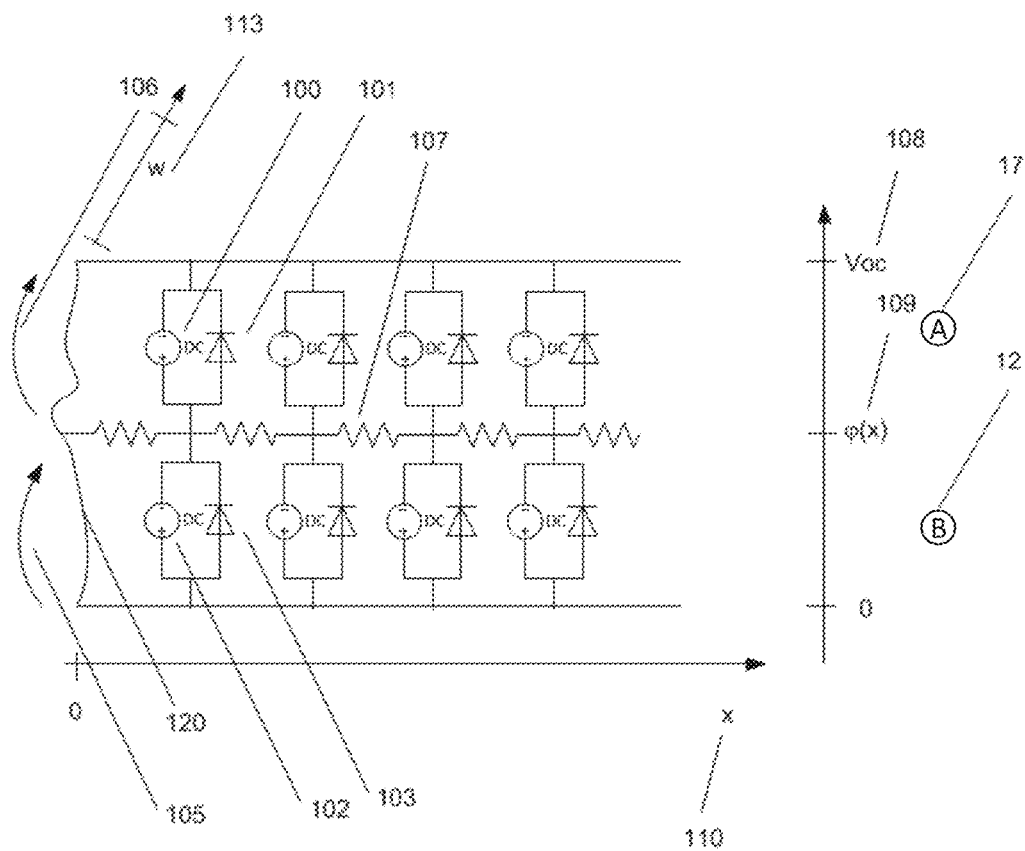
FIG. 3 shows a circuit diagram of a simplified two-dimensional network model of a dual junction solar cell.

The basic formation of the contrast of a mechanical defect in the photoluminescence image of a multi-junction cell and the basis behind the present disclosure can be understood by looking at a dual junction cell 11. An advantage of using a photoluminescence approach is that the photocurrents $J_{ph}^1$, $J_{ph}^2$ can be adjusted separately for each junction, while in electroluminescence the externally applied current is always the same in all p-n junctions. In FIG. 3 a simplified network model is illustrated. It is a two-dimensional model, showing a cross-section through the cell normal to a mechanical defect 120 indicated on the left.

The cell consists of two p-n junctions A 17 and B 12. Each node is described by a simplified solar cell consisting of a current source 100, 102 and a diode 101, 103 in parallel. The vertical current J through each node in layer A is thus given by $$J^1 = J_{ph}^1 - J_0^1 \exp(e(V_{oc}-\varphi)/n_1 kT) \quad (1)$$

Where e, k and T are the electron charge, the Boltzmann constant and the temperature respectively. n denotes the diode ideality factor, $J_{ph}$ the photocurrent and $J_0$ the dark saturation current. For layer B an equivalent equation is valid.

$$J^2 = J_{ph}^2 - J_0^2 \exp(e\varphi/n_2 kT) \quad (2)$$

The photoluminescence intensity T that is recorded is a direct measure of the voltage at each diode. The following equations hold (cf. U. Rau, Phys. Rev. B 76, 085303 (2007)):

$$\Phi^1 = K^1 \exp(e(V_{oc}-\varphi/kT))$$

$$\Phi^2 = K^2 \exp(e\varphi/kT) \quad (3)$$

Here, $\Phi^1$ describes the photoluminescence intensity emitted by the topmost p-n junction A 17 (subcell A) and $\Phi^2$ describes the photoluminescence intensity emitted by the p-n junction B 12 (subcell B) adjacent to the topmost p-n junction A 17. In the following, an index 1 is used for the p-n junction A and an index 2 is used for the p-n junction B.

The constant K summarizes the characteristic parameters of the detection system. The elements 107 in the solar cell between the subcell A 17 and B 12 provide a path for lateral current transport with a given sheet resistance r (in units of Ohm). The cell rearside is fully metallized and thus at a common potential of 0 V. Similarly, on the frontside the gridfinger spacing is much narrower than any spatial effect of the cell cracks on the luminescence distribution. Therefore also, the frontside is at a constant potential, defined by the open circuit voltage Voc 108 of the cell sufficiently far away from the cell crack. $V_{oc}$ is the sum of the open circuit voltages of layer A, $V_{oc}^1$ and layer B, $V_{oc}^2$.

By applying Kirchhoff's laws for the current and voltage at each node, the following differential equation can be derived for the voltage $\varphi$ at the intermediate layer as a function of the position x:

$$\frac{\partial^2 \varphi}{\partial x^2} = r[J_0^2 \exp(e\varphi(x)/n_2 kT) - J_{ph}^2 - J_0^1 \exp(e(V_{oc} - \varphi(x))/n_1 kT) + J_{ph}^1] \quad (4)$$

At a distance x 110 sufficiently far away from the site of the crack located at x=0, each node is at its respective open circuit voltage $V_{oc}^1$ and $V_{oc}^2$. By defining $$y = \varphi - V_{oc}^2 \quad (5)$$

and using a linear approximation for the exponential terms in the preceding equation 4, taking into account that under open circuit condition the relations $J_{ph}^1 = J_0^1 \exp(eV_{oc}^1/n_1 kT)$ and $J_{ph}^2 = J_0^2 \exp(eV_{oc}^2/n_2 kT)$ hold, the following equation is derived $$\frac{\partial^2 y}{\partial x^2} = r\left[J_{ph}^2 \frac{e}{n_2 kT} + J_{ph}^1 \frac{e}{n_1 kT}\right] y \quad (6)$$

The new semiconductor surface created at the crack site results in a recombination current $I_s^1$ 106 and $I_s^2$ 105 across the crack site. This is the physical reason why mechanical defects are visible in luminescence images (cf. C. G. Zimmermann, J. Appl. Phys. 100, 023714 (2006)). Its magnitude is given by $$I_s^1 = \frac{1}{2} w e S_1 n_i^1 t_1 \exp\left(\frac{e(V_{oc} - \varphi(0))}{2kT}\right) \quad (7)$$

$$I_s^2 = \frac{1}{2} w e S_2 n_i^2 t_2 \exp\left(\frac{e\varphi(0)}{2kT}\right)$$

where S denotes the surface recombination velocity, $n_i$ the intrinsic carrier density and t the thickness of the p-n junction. w is an arbitrary distance 113 parallel to the crack. The difference between the two surface recombination currents results in a lateral current between the two layers A and B, which is proportional to the first derivative of the local voltage $\varphi$:

$$I_s^2 - I_s^1 = \frac{w}{r} \left. \frac{\partial \varphi}{\partial x} \right|_{x=0} \quad (8)$$

Evaluating this equation further, again using a linear approximation for the exponential terms, results in $$\left. \frac{\partial y}{\partial x} \right|_{x=0} = r\left[C_2 - C_1 + \frac{e}{2kT}(C_1 + C_2) y(0)\right] \quad (9)$$

with $$C_j = \frac{1}{2} e S_j n_i^j t_j \left(\frac{J_{ph}^j}{J_0^j}\right)^{n_j/2} ; j = 1, 2 \quad (10)$$

Solving equation 6 with the boundary condition according to equation 9 yields the voltage y as a function of position x:

$$y(x) = \frac{C_1 - C_2}{\frac{e}{2kT}(C_1 + C_2) + \sqrt{\frac{e}{rkT}\left(\frac{J_{ph}^1}{n_1} + \frac{J_{ph}^2}{n_2}\right)}} \exp\left(-\sqrt{r\frac{e}{kT}\left(\frac{J_{ph}^1}{n_1} + \frac{J_{ph}^2}{n_2}\right)} x\right) \quad (11)$$

The photoluminescence intensity $\Phi$ is thus given (again in linear approximation) according to equation 3 by:

$$\Phi^1(x) = \Phi_0^1\left(1 - \frac{e}{kT} y(x)\right) \quad (12)$$

$$\Phi^2(x) = \Phi_0^2\left(1 + \frac{e}{kT} y(x)\right)$$

$$\Phi_0^1 = K^1 \exp(eV_{oc}^1/kT)$$

and $$\Phi_0^2 = K^2 \exp(eV_{oc}^2/kT)$$

denote the photoluminescence intensities away from the crack in undisturbed areas of the cell.

This model is applied to the first two junctions of a triple junction III-V solar cell. There layer A is a $Ga_{0.5}In_{0.5}P$ cell and layer B is a GaAs cell. The influence of the bottom Ge cell is neglected. Their typical parameters are summarized in Table 1:

TABLE 1

Typical parameters of a Ga0.5In0.5P cell as layer A and a GaAs cell as layer B.

| layer | J0 [A/cm2] | n | thickness t [µm] | S [cm/s] | ni [cm-3] | r [Ohm] |
|---|---|---|---|---|---|---|
| A | 5.55E-24 | 1.12 | 0.6 | 8.00E+04 | 3.00E+03 | |
| B | 4.95E-19 | 1.03 | 1.5 | 5.50E+05 | 2.10E+06 | 1.70E+02 |

Figure 4:
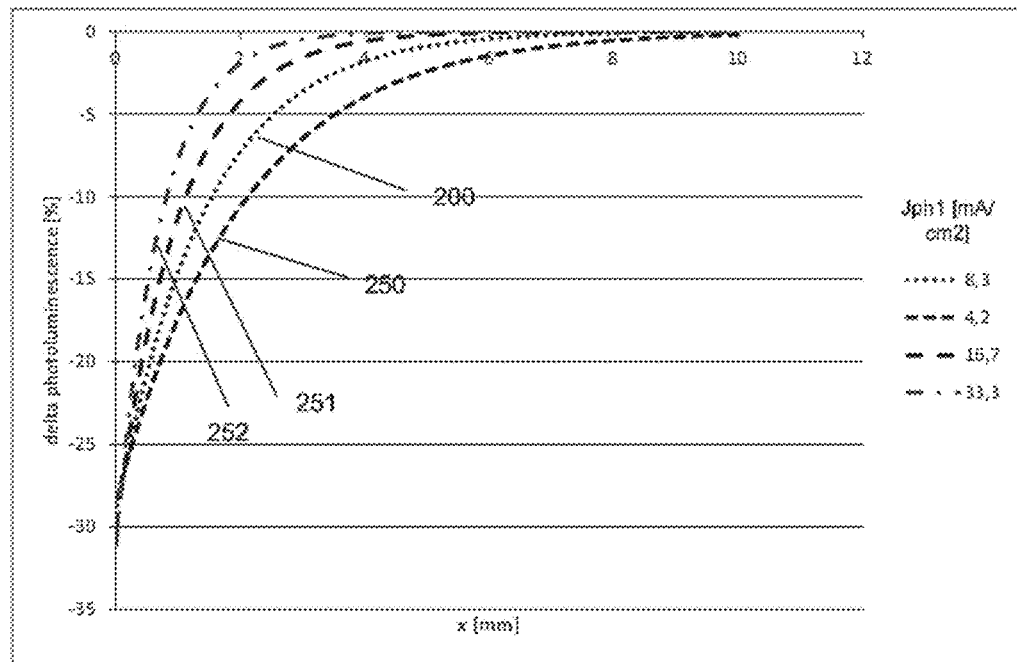
FIG. 4 shows a diagram indicating a change in the photoluminescence intensity emitted by a topmost p-n junction due to the presence of a mechanical defect for four different illumination intensity levels of the topmost p-n junction.

With these parameters, the relative deviation $[\Phi(x) - \Phi 0]/\Phi 0$ of the photoluminescence intensity for layer A is plotted as a function of the distance x away from the crack located at x=0 in FIG. 4. No other illumination is present, i.e. $J_{ph}^2 = 0$. Curve 200 is showing the distribution for a photocurrent $J_{ph}^1$ of 8 mA/cm2. The photoluminescence decreases with a characteristic exponential function towards the crack. The physics behind the contrast formation can be understood by considering that the new semiconductor surface created through the cell crack acts as a recombination site. The recombination current has to flow laterally along the path 107 between layer A and B. The associated voltage drop decreases the voltage at the p-n junctions along this path and leads to the characteristic contrast. In this fashion a crack affects the photoluminescence distribution over a ≈2 mm length scale, using the −10% point for evaluation. This feature can be used to easily identify the crack even in a fairly low resolution image. Since in a multi-junction cell all subcells are mechanically coupled, a crack will vertically penetrate all junctions. Therefore, any one junction can be used to identify mechanical defects.

It should be pointed out that the method outlined also applies to all other features in the cell, which locally result in a dissipation of current. One example of these electrical defects are growth defects, which are areas of disturbed, non-epitaxial growth. They will affect the photoluminescence contrast in a similar way. In the photoluminescence image they can be distinguished from mechanical defects by their shape. Mechanical defects are line-like, essential 1-dimensional, whereas growth defects have a rounded, 2-dimensional appearance.

In case of illuminating only one p-n junction there is a limited possibility of adjusting the contrast of the defect. For a cell with an ideality factor n=1, the contrast a x=0 is not affected by changing $J_{ph}^1$ according to Equation 11, since the $J_{ph}^1$ dependence in the pre-exponential factor cancels out, and only the distance over which a change in contrast occurs can be adjusted in a limited range according to the square root dependence on $J_{ph}^1$ in the exponential term. This is visualized in FIG. 4 as well for 3 cases where $J_{ph}^1$ is doubled 251 or quadrupled 252 compared to curve 200, or cut in half 250. Despite the huge change in illumination level, the ability to affect the length over which the photoluminescence distribution is affected, for example defined at the −10% point, is very limited. In addition, there are practical limitations: going to very high illumination levels like the 33 mA/cm² curve requires very high power light sources, whereas decreasing the illumination, for example to the 4 mA/cm2 level, decreases the overall photoluminescence intensity and increases the required sensitivity of the detection system.

Figure 5:
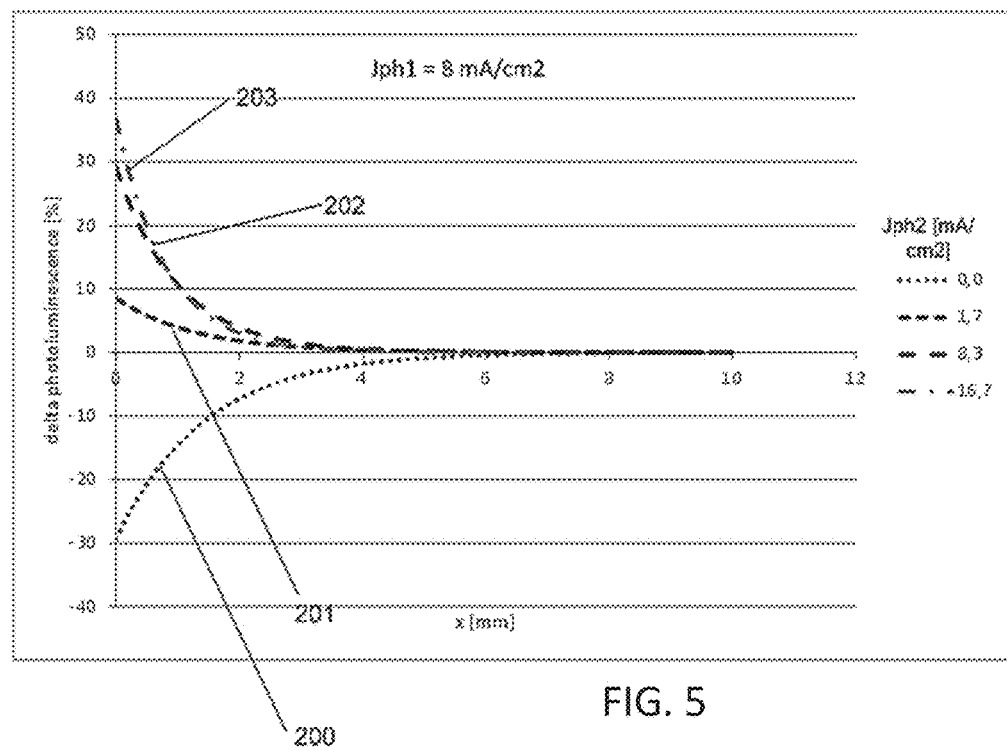
FIG. 5 shows a diagram indicating a change in the photoluminescence intensity emitted by the topmost p-n junction due to the presence of a mechanical defect for four different illumination intensity levels of the second-from-top p-n junction.

Layer B, however, can be illuminated in addition. This is shown in FIG. 5 for corresponding photocurrents $J_{ph}^2$ of 1.7 mA/cm² (curve 201), 8.3 mA/cm² (curve 202) and 16.7 mA/cm² (curve 203). As can be seen from these graphs, by illuminating layer B as well, the contrast of the crack in the photoluminescence image of layer A can be altered, and in this example even reversed. This is due to the fact that for the given semiconductor parameters, in particular the surface recombination velocity S, the recombination current across the crack in layer B is higher than in layer A. Therefore, even for moderate illumination of layer B, the net current flow across the intermediate layer 107 is reversed, resulting in an increase of the photoluminescence signal towards the crack.

Figure 6:
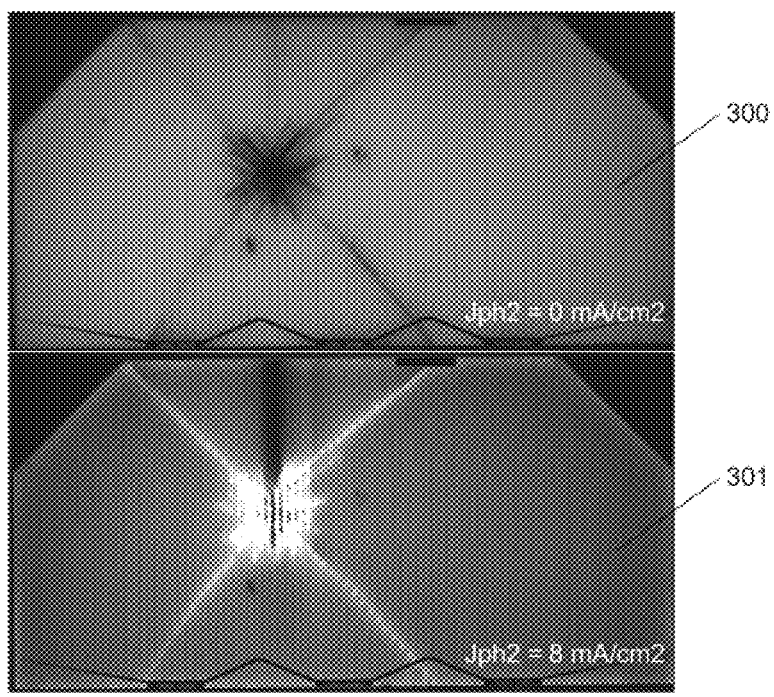
FIG. 6 shows top cell photoluminescence images belonging to a Ga0.5In0.5P/GaAs/Ge triple junction solar cell for only top cell illumination (300) and top and middle cell illumination (301), wherein the top cell illumination created a photocurrent of Jph1 of 8 mA/cm2 in both the upper section 300 and the lower section 301.

In FIG. 6 top cell photoluminescence images of a triple junction cell are shown, both acquired at photocurrent in the top cell of 8 mA/cm². In image 300 no other illumination is present, and the crack is identified by the dark contrast in accordance with this model. In image 301, the middle cell (layer B) is illuminated with a photocurrent of 8 mA/cm² as well, and the contrast of the crack in the top cell image is reversed.

Figure 7:
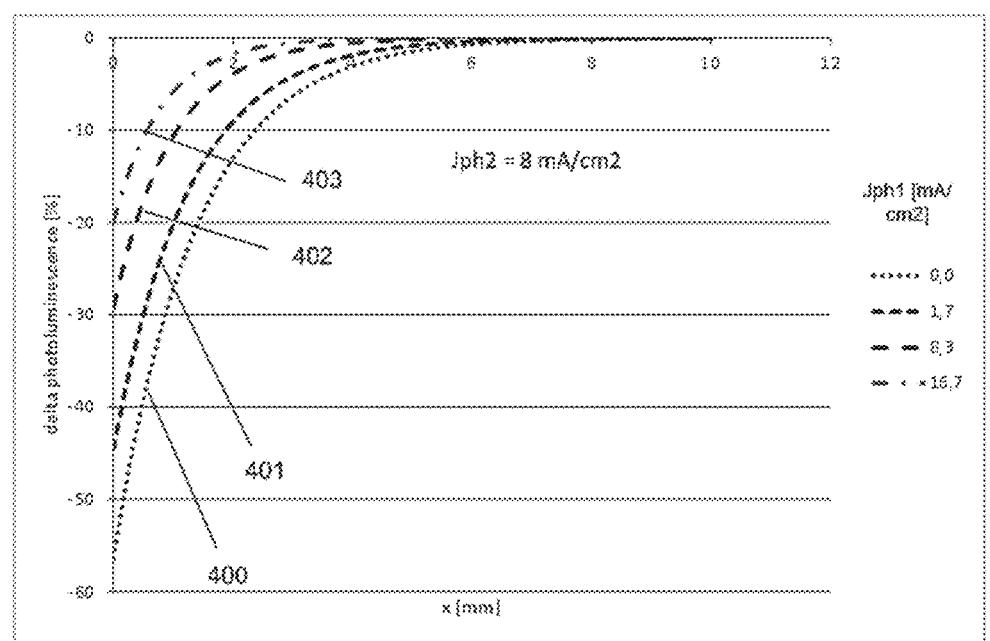
FIG. 7 shows a diagram indicating a change in the photoluminescence intensity emitted by the second-fromtop p-n junction due to the presence of a mechanical defect for four different illumination intensity levels of the topmost p-n junction.

The behavior of layer B is similar. The expected contrast according to the model is illustrated in FIG. 7. Without any additional illumination of layer A, the crack creates a much more pronounced contrast as in layer A, owing to the higher surface recombination at the crack for this layer. This is shown in curve 400. With additional illumination of the top cell, this contrast can be decreased by the same mechanism as for layer A. Due to the additional recombination at the crack in layer A, less current has to flow laterally along the path 107 and therefore the voltage drop is smaller. This is illustrated in curves 401, 402 and 403.

Figure 8:
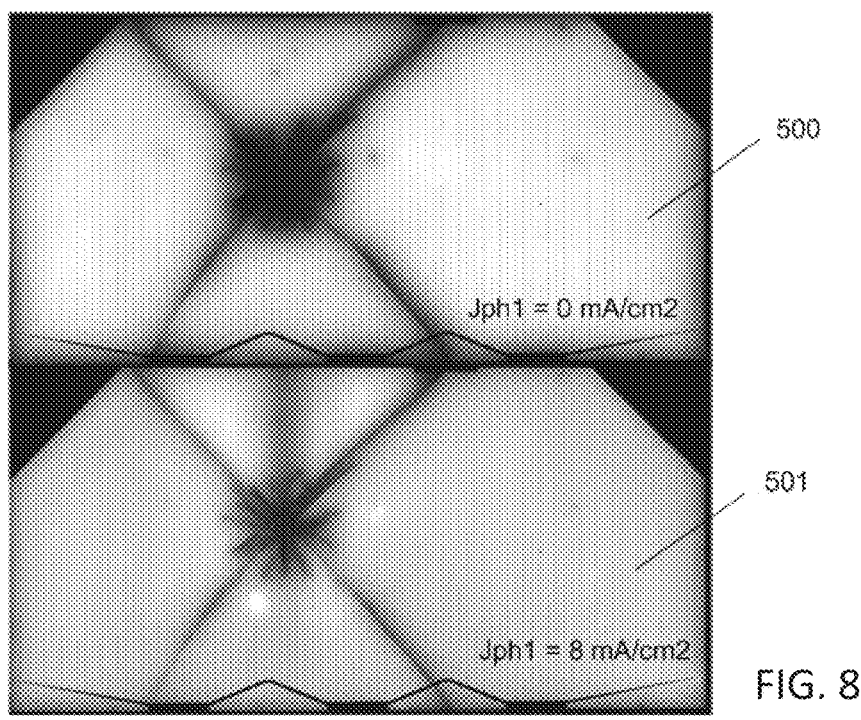
FIG. 8 shows middle cell photoluminescence images belonging to a Ga0.5In0.5P/GaAs/Ge triple junction solar cell for only middle cell illumination (500) and top and middle cell illumination (501), wherein the middle cell illumination created a photocurrent of Jph2 of 8 mA/cm2 in both the upper section 500 and the lower section 501.

The resulting middle cell photoluminescence images acquired at a photocurrent $J_{ph}^2$ of 8 mA/cm² is shown in FIG. 8. In image 500 no additional top cell illumination is present, resulting in a very strong contrast, as predicted. Finer details of the crack pattern, especially in the center part of the image, are smeared out. As shown in curve 400, the crack affects the photoluminescence distribution over considerable distance: ≈3 mm away from the crack the intensity is still reduced by 10%. In image 501 the top cell is illuminated in addition creating a photocurrent of $J_{ph}^1$ of 8 mA/cm² there. The contrast is not as pronounced any more, resulting in a better resolved crack pattern. This is in line with curve 402, where the 10% contrast point is now only ≈1 mm away from the crack.

Therefore, illuminating a subcell in a multi-junction cell stack, adjacent to the cell whose photoluminescence emission is imaged, provides a possibility to tune the contrast of a mechanical defect in a wide range according to the needs of the detection system.

Furthermore, the photoluminescence emission in the remainder of the cell, at a sufficient distance from the crack, is not affected at all by the illumination level of the adjacent cell. This provides an excellent opportunity in isolating solely the cell crack in the photoluminescence image.

Figure 9:
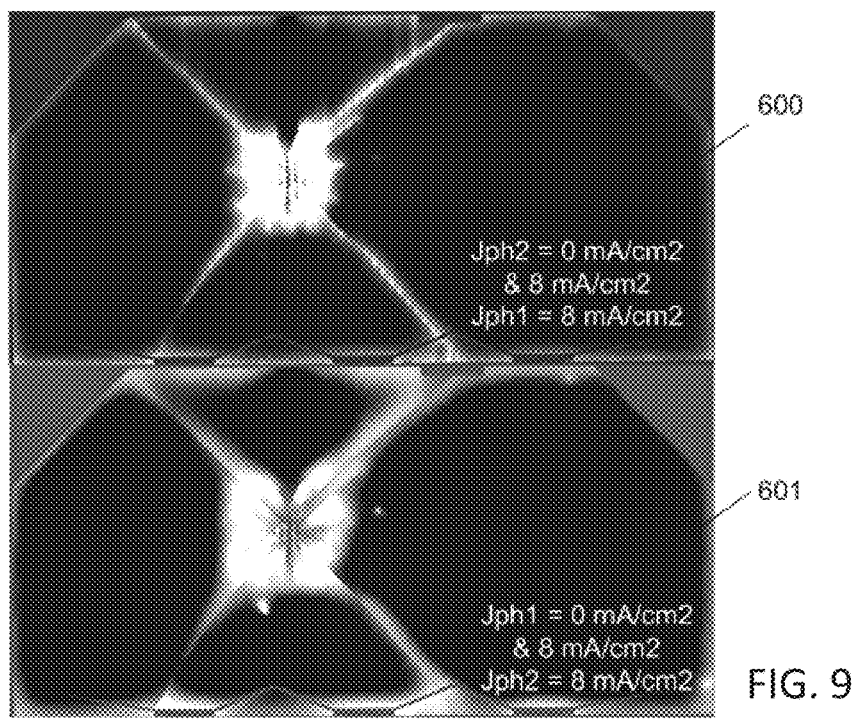
FIG. 9 shows difference photoluminescence images obtained on a Ga0.5In0.5P/GaAs/Ge triple junction solar cell, wherein image 600 is a top cell image obtained as image 300 subtracted from image 301 and image 601 is a middle cell image obtained as image 500 subtracted from image 501.

If again the top cell photoluminescence image of a $Ga_{0.5}In_{0.5}P/GaAs/Ge$ cell, acquired at $J_{ph}^1$ of 8 mA/cm² without any illumination of the middle cell, as shown in image 300, is subtracted from the top cell photoluminescence image at $J_{ph}^1$ of 8 mA/cm² with additional illumination of the middle cell $J_{ph}^2$ of 8 mA/cm², as shown in image 301, only the features of the cell crack remain in the image. This resulting image 600 is shown in FIG. 9. The same can be done with middle cell images acquired for different top cell illuminations. Image 601 depicts image 500, acquired without top cell illumination, subtracted from image 501, acquired with $J_{ph}^1$ of 8 mA/cm² top cell illumination. Images 600 and 601 are particularly suitable for automated image processing algorithms aimed at detecting defects in the photoluminescence image since a clear difference in contrast exists between the defect and the remainder of the cell. Simple operations like thresholding the image are suitable to extract the defect pattern.

For all the suggested methods which involve the illumination of at least two adjacent junctions, various illumination levels of the adjacent subcell not imaged can be used in finding the optimum image for an automated defect detection algorithm. For example, an image processing algorithm that analyses the image of one junction can have an active feedback loop that adjusts the illumination level of the junction not imaged. In addition, the analysis of the image cannot only be performed spatially by looking at changes in photoluminescence intensity with respect to the position on the cell, but also in the time domain. For example, the illumination level of the adjacent cell not imaged can be ramped up with a certain time constant. The photoluminescence image of the cell monitored is then analyzed for all pixels whose intensity changes with time. The fact that there is a correlation in the change in photoluminescence intensity as a function of time with the change in illumination intensity of the junction not imaged can be exploited in addition.

It should be pointed out here as well that the method outlined also applies to all other features in the cell, which locally result in a dissipation of current. One example of these electrical defects are growth defects, which are areas of disturbed, non-epitaxial growth. They will affect the photoluminescence contrast in a similar way. In case they penetrate more than one junction, all junctions affected by the electrical defect can be used to adjust the contrast identically to the case of mechanical defects.

The methods of a photoluminescence based crack detection for multi-junction cells described in this disclosure are based on the realizations outlined above. The methods are applicable to all multi-junction cell architectures which have at least two p-n junctions (subcells or layers). The methods are preferably applicable to junctions made of direct bandgap semiconductors, since those emit a strong photoluminescence signal.

Figure 10:
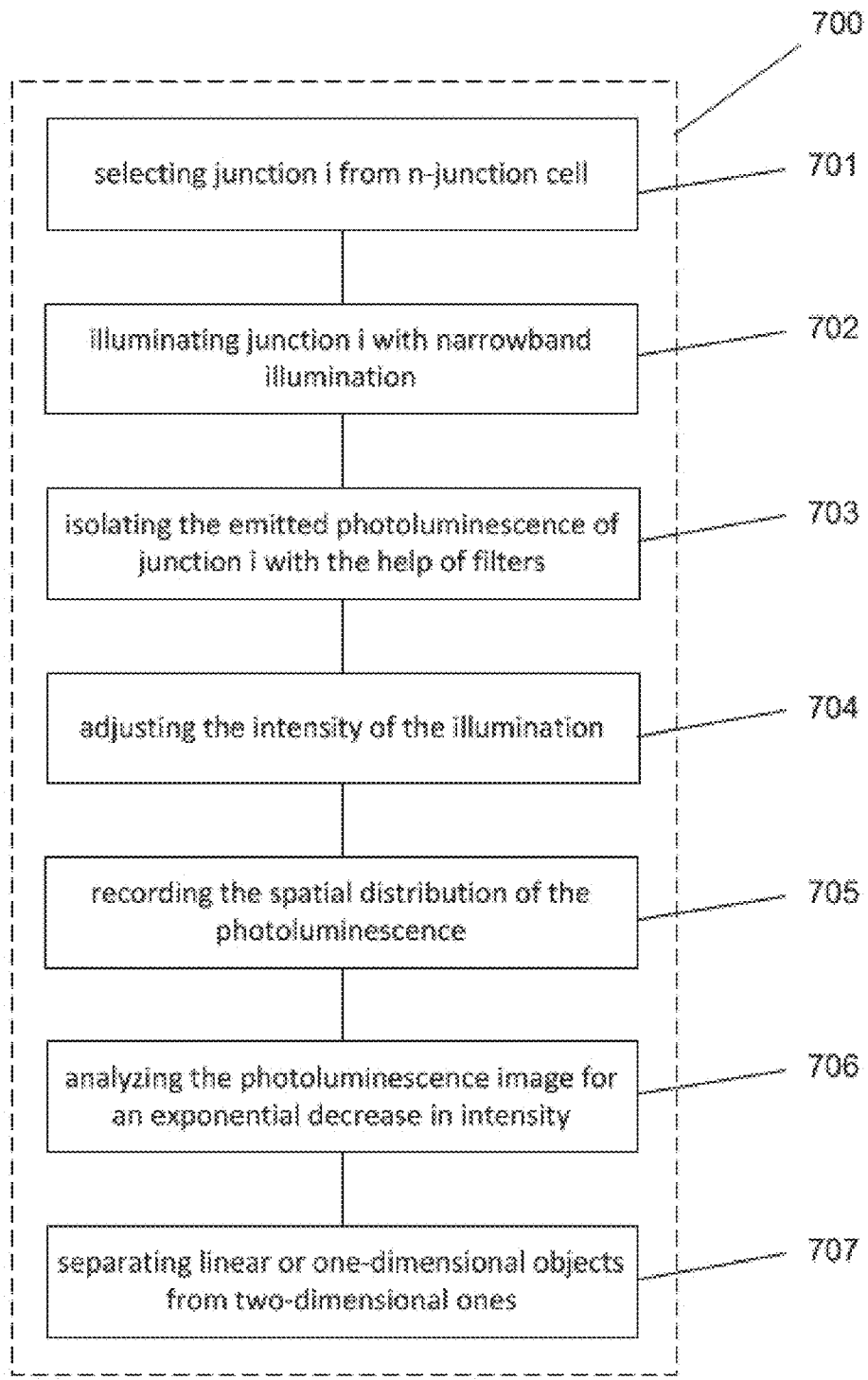
FIG. 10 shows a flowchart of an exemplary method for detecting a defect in a multi-junction solar cell by exciting a p-n junction i.

In a first basic implementation 700, a method for detecting a defect in a multi-junction solar cell consists of the following steps, as shown in FIG. 10. As a first step 701, one junction i out of the n junction device is selected. For most applications the individual junctions in a multi-junction cell are mechanically coupled. In cells consisting of III-V semiconductors, for example, all junctions are grown epitaxially as essentially one big crystal. In these cases, a cell crack that is created by an external stress on the cell will penetrate all junctions, which are only several μm thin. In these cases, due to the mechanical coupling, any one junction can be used for detection of the mechanical defect. The junction to be used can therefore be selected based on the following considerations:

i) The magnitude of the surface recombination velocity of the semiconductor material used for junction i. The higher this parameter is, the stronger the contrast as outlined before.

ii) The wavelength range in which junction i emits photoluminescence. Junctions which emit outside the visible wavelength range, for example in the infrared, are preferable if the inspection is to be performed under ambient light conditions, which can be easily blocked in this case.

iii) The wavelength range in which junction i absorbs radiation. The availability of suitable light sources for the chosen subcell as well as suitable optical detectors for the emitted photoluminescence radiation are to be taken into consideration as well.

In addition, the spectral distribution of the light used for illuminating junction i 702 should not have any contribution around the wavelength $\lambda_i = E_g^i / hc$, where junction i emits photoluminescence, as it is customary for all photoluminescence applications. $E_g^i$ denotes the bandgap energy of junction i. Ideally the distribution of the illuminating light is homogeneous across the cell area.

The emitted photoluminescence from junction i, occurring around $\lambda_i$, is then separated from the exciting wavelength as well as other disturbing factors like ambient light or photoluminescence created through optical coupling into other junctions with the help of appropriate filters in step 703.

As a next step 704 the intensity of the illuminating light is adjusted such that the photocurrent $J_{ph}^i$ generated in junction i is around the short circuit current of the cell under its normal operating conditions. For cells operated under the air mass zero (AM0) or air mass 1.5 (AM1.5) sun spectrum $J_{ph}^i$ is preferably between 5-100 mA/cm$^2$, and more preferably between 10-20 mA/cm$^2$. For devices designed to be operated under concentrated sunlight with a concentration factor c, the range of $J_{ph}^i$ can also be extended by a factor c.

The photoluminescence is recorded spatially resolved 705 with the help of appropriate optical detectors like CCD or CMOS cameras, for example based on Si, InGaAs or HgCdTe, depending on the required spectral sensitivity. Alternatively, other detectors like the small diameter fiber of a spectrometer can be used to scan the cell area.

In step 706 the image is then analyzed for an exponentially varying contrast. According to the model presented here, the change in contrast along a line normal to the path of the crack follows approximately a $-Ae^{-kx}$ dependence, where x denotes the distance along this line from the crack and A and k are constants. The contrast far away from the defect is unaffected. It decreases exponentially with $e^{-kx}$ towards the crack, where it is decreased by A. As demonstrated, in the example of images 300, 301, 500, and 501, the mechanical defect is easily identified visually by an operator. The exponential variation of the contrast, however, can be used as the basis of automated imaging processing algorithms 707. Other features in a cell, most notably shunts caused by growth defects or the cell edge, will cause a similar contrast. These elements can be easily distinguished by their shapes and, respectively, position. Shunts caused by growth defects have a rounded, 2-dimensional shape, in contrast to the linear, one-dimensional shape of mechanical defects. The cell edge, which also generates image contrast by dissipating current similar to a mechanical defect, can be easily removed from the analysis based on the absolute position of the cell.

Figure 11:
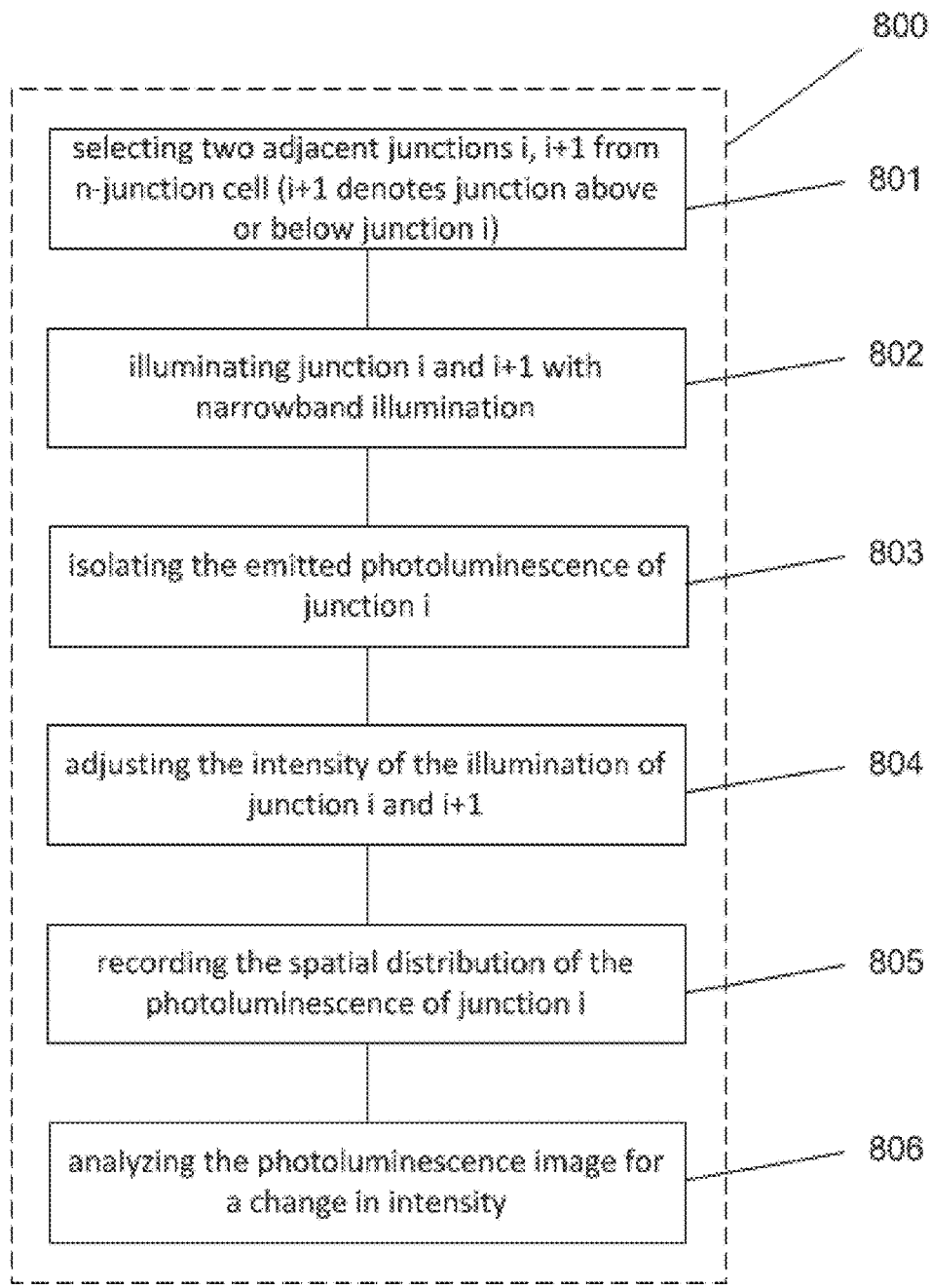
FIG. 11 shows a flowchart of an exemplary method for detecting a defect in a multi-junction solar cell by exciting a p-n junction i and an adjacent p-n junction i+1.

Further, FIG. 11 shows a second implementation of a method for detecting a defect in a multi-junction solar cell according to the present disclosure. The second implementation 800, as shown in FIG. 11, comprises selecting one junction i as before, together with the adjacent junction above or below this junction (in the following just labeled i+1) 801. For the selection of junctions i and i+1, the same arguments mentioned in conjunction with step 701 are valid. Both junctions i and i+1 are illuminated with narrowband illumination which again fulfills the requirements of step 702 and, in addition, in this case is largely only absorbed in either junction i or i+1. The photoluminescence of junction i is isolated again with the help of suitable filters 803. The intensity of the illumination of junction i, resulting in a photocurrent $J_{ph}^i$, and i+1, resulting in $J_{ph}^{i+1}$, is adjusted 804 and the photoluminescence image of junction i is acquired 805. The adjustment is made such that the contrast of the mechanical defect in the photoluminescence image is optimized for the capabilities of the optical detector or image analysis method. Preferably $J_{ph}^{i+1}$ is adjusted such that the width of the mechanical defect in the photoluminescence image, defined by the points on a line normal to the crack where the intensity deviates only 10% from its intensity in unaffected areas is in the range 0.1-10 mm, preferably 0.3-6 mm and more preferably 0.5-3 mm. Preferably $J_{ph}^i$ and $J_{ph}^{i+1}$ are between 5-100 mA/cm$^2$, more preferably between 10-20 mA/cm$^2$.

It is obvious to persons skilled in the art that this method can be easily extended to illuminating more than two adjacent cells. The main requirement is that all illuminated subcells are adjacent to the subcell i of interest. The effect of optical coupling, i.e., the effect that charge carriers in one externally illuminated junction recombine and illuminate the junction underneath can be used to relax this requirement. If one junction receives significant amount of radiation via optical coupling, this radiation serves the role of an external illumination. Since this illumination cannot be adjusted externally, however, the external illumination of at least the cell underneath is required still.

In some cases, it can be beneficial not to illuminate all junctions. For example, in the case of a 4 junction cell that contains a severe shunt, illuminating all cells will result in a significantly reduced luminescence, since the shunt short circuits the entire cell by providing a low resistance path between top and rear side metallization. This can be avoided, if only two junctions are selected and illuminated for this method, for example the second and third junction. The non-illuminated top cell prevents the shunt from affecting the biasing point of the overall cell, which is still in open circuit conditions in the latter case.

The recorded photoluminescence image is then analyzed 806 manually or automatically for an abrupt change in intensity. According to the theory presented, the change in contrast along a line normal to the path of the crack follows also under these conditions approximately a $-Ae^{-kx}$ dependence, where x denotes the distance along this line from the crack and A and k are constants. In this case A can also be negative, i.e., the contrast increases exponentially with $e^{-kx}$ towards the location of the crack. This approximate functional dependence can be conveniently used in automated detection algorithms.

It is also possible to implement a dynamic image processing algorithm. There the illumination level of junction i+1 is set to different values, while the photoluminescence image is analyzed for local changes in contrast correlated with a variation in $J_{ph}^{i+1}$. Since only the contrast of defects is affected by changes in $J_{ph}^{i+1}$, but not the remainder of the cell, defects are easily identified in this way. The image processing algorithm only has to identify pixels, that change in value with changing $J_{ph}^{i+1}$. $J_{ph}^{i+1}$ can for example, be increased stepwise from 0 mA/cm$^2$ to $2 \times J_{ph}^{i}$. This can be implemented, for example, by ramping up the illumination of junction i+1 with a constant rate, while recording the photoluminescence images of junction i. It is also possible to implement a feedback loop, which allows the image processing algorithm to change the illumination level of junction i+1 during continuous image acquisition of junction i to different values.

As before, other features in a cell, most notably shunts caused by growth defects or the cell edge will cause a similar contrast. These elements, can be easily distinguished by their shape respectively position. Electrical defects caused by growth defects have a rounded, 2-dimensional shape, in contrast to the linear, one-dimensional shape of mechanical defects. The cell edge can be easily removed from the analysis based on the absolute position of the cell.

Figure 12:
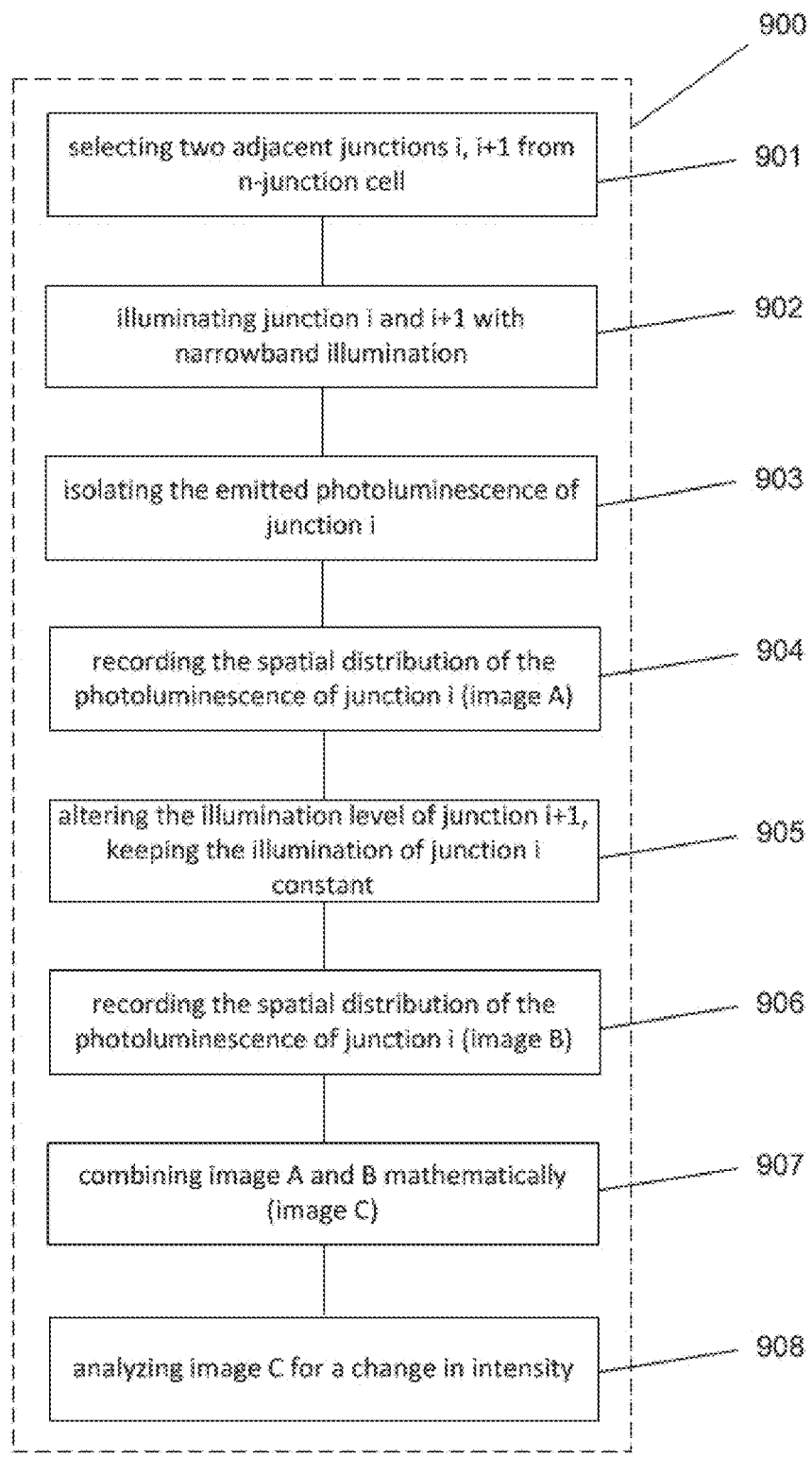
FIG. 12 shows a flowchart of an exemplary method for detecting a defect in a multi-junction solar cell by exciting a p-n junction i and an adjacent p-n junction i+1 and by generating a combined image.

A further implementation of a method for detecting a defect in a multi-junction solar cell is shown in FIG. 12. This method is again based on selecting at least two adjacent junctions i, i+1 901, which are all illuminated by narrowband illumination 902. The photoluminescence of junction i is isolated with the help of suitable filters 903. The photoluminescence image A of one junction i is acquired for a given setting of illumination levels of all junctions 904. Then the illumination level of junction i is kept constant, and the illumination level of at least one other illuminated cell is changed 905. Again the photoluminescence image B of junction i is recorded 906. Subsequently the images A and B are combined mathematically. Preferably one image is subtracted from the other, since this removes all contrast from unaffected areas of the cell 907. This image is then analyzed for abrupt contrast variations 908. Suitable illumination levels create photocurrents between 5-20 mA/cm$^2$ in each illuminated junction. The difference in illumination levels between image A and image B results in a change in photocurrent in one of the illuminated junctions, except junction I, in a 1-20 mA/cm$^2$, more preferably in a 5-10 mA/cm$^2$ range.

Features in this image that can be detected are electrical defects like shunts or the cell edge, as well as mechanical defects. Mechanical defects can be separated from electrical ones, caused, e.g., by growth defects, based on their shape. One-dimensional, linear objects are attributed to mechanical defects, whereas rounded, two dimensional objects are electrically active growth defects. The image analysis can be performed purely visually. Alternatively, this method, which enhances the contrast of the defects significantly, can be used to generate images most suitable for subsequent image processing for automatic defect detection. Simple image processing steps, like thresholding the image, are adequate for this purpose. This is not the case if a standard photoluminescence image is used.

In addition, the image processing can not only be performed statically in one difference image, but also dynamically by identifying areas in the difference image that change while $J_{ph}^{i+1}$ is changed. It can, for example, be based on a series of difference images acquired with constant illumination of junction i, generating a photocurrent $J_{ph}^{i}$, and a stepwise increase in the illumination of junction i+1, for example from 0 mA/cm2 to $2 \times J_{ph}^{i}$. This can be implemented, for example, by ramping up the illumination of junction i+1 with a constant rate, while recording the photoluminescence images of junction i. It is also possible to implement a feedback loop, which allows the image processing algorithm to change the illumination level of junction i+1 during continuous image acquisition of junction i to different values. In this fashion the image analysis algorithm becomes very simple. It only has to identify pixels in the image which vary in contrast with changing $J_{ph}^{i+1}$.

Figure 13:
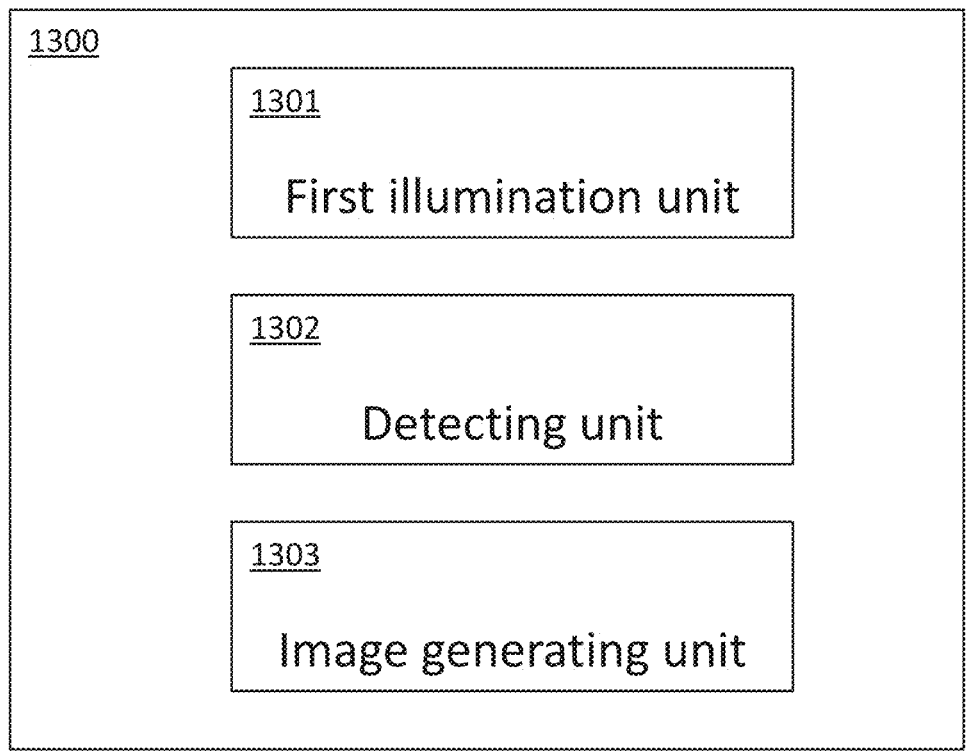
FIG. 13 shows a schematic block diagram of an apparatus for detecting a defect in a multi-junction solar cell.

FIG. 13 shows a general arrangement of an apparatus 1300 for detecting a defect in a multi-junction solar cell comprising at least two vertically stacked p-n junctions. The apparatus 1300 comprises a first illumination unit 1301 configured to excite a first p-n junction of the at least two vertically stacked p-n junctions by illuminating the solar cell with excitation light in a first excitation wavelength range. The apparatus 1300 further comprises a detecting unit 1302 configured to detect photoluminescence light emitted by photoluminescence of the first p-n junction. The apparatus 1300 further comprises an image generating unit 1303 configured to generate a spatially resolved first photoluminescence image of the photoluminescence light emitted by the first p-n junction. The apparatus 1300 is configured to carry out any of the methods 700, 800, and 900 described above.

Figure 14:
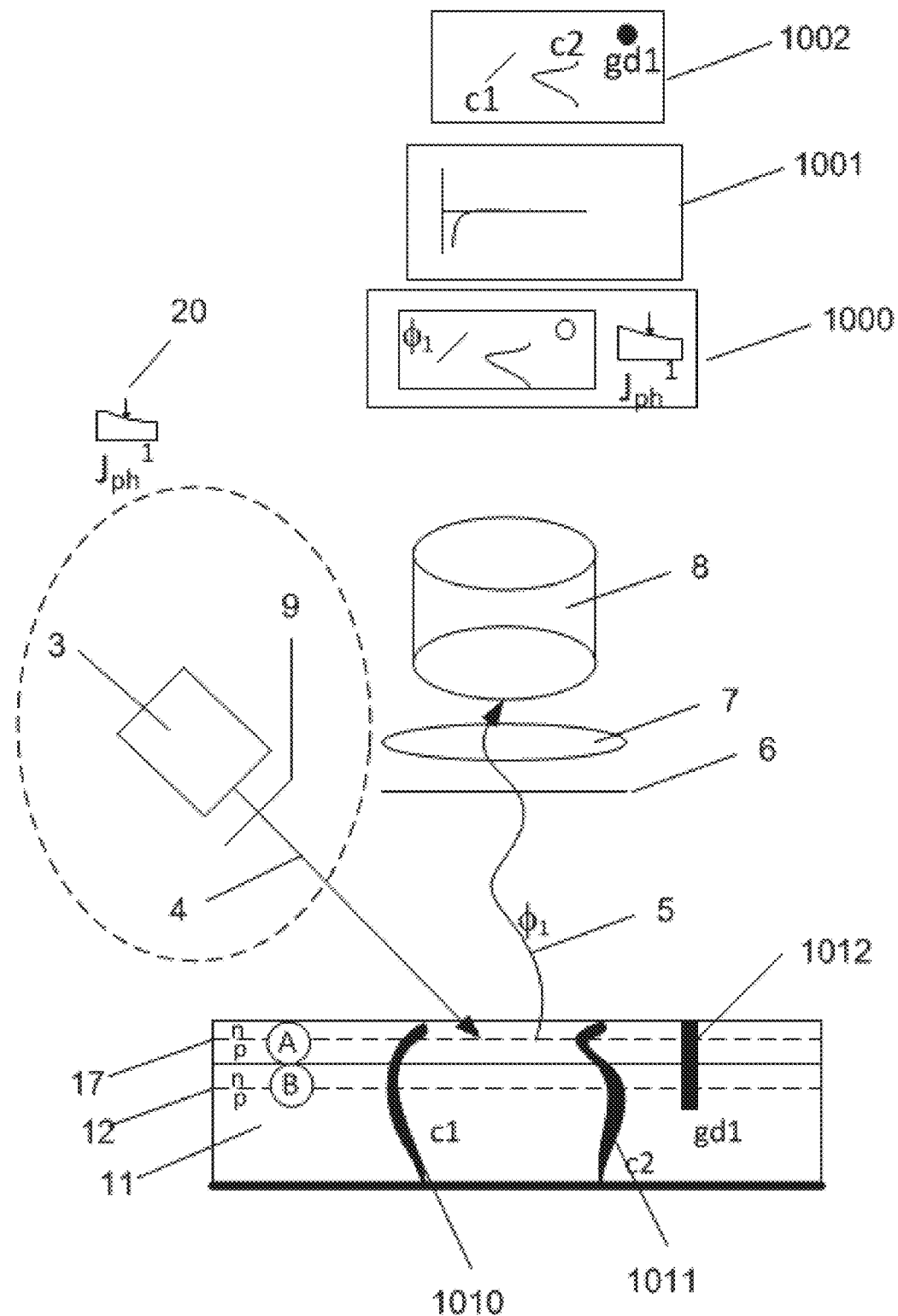
FIG. 14 shows a schematic representation of an apparatus for detecting a defect in a multi-junction solar cell that might be used for carrying out the method of FIG. 10.
Figure 15:
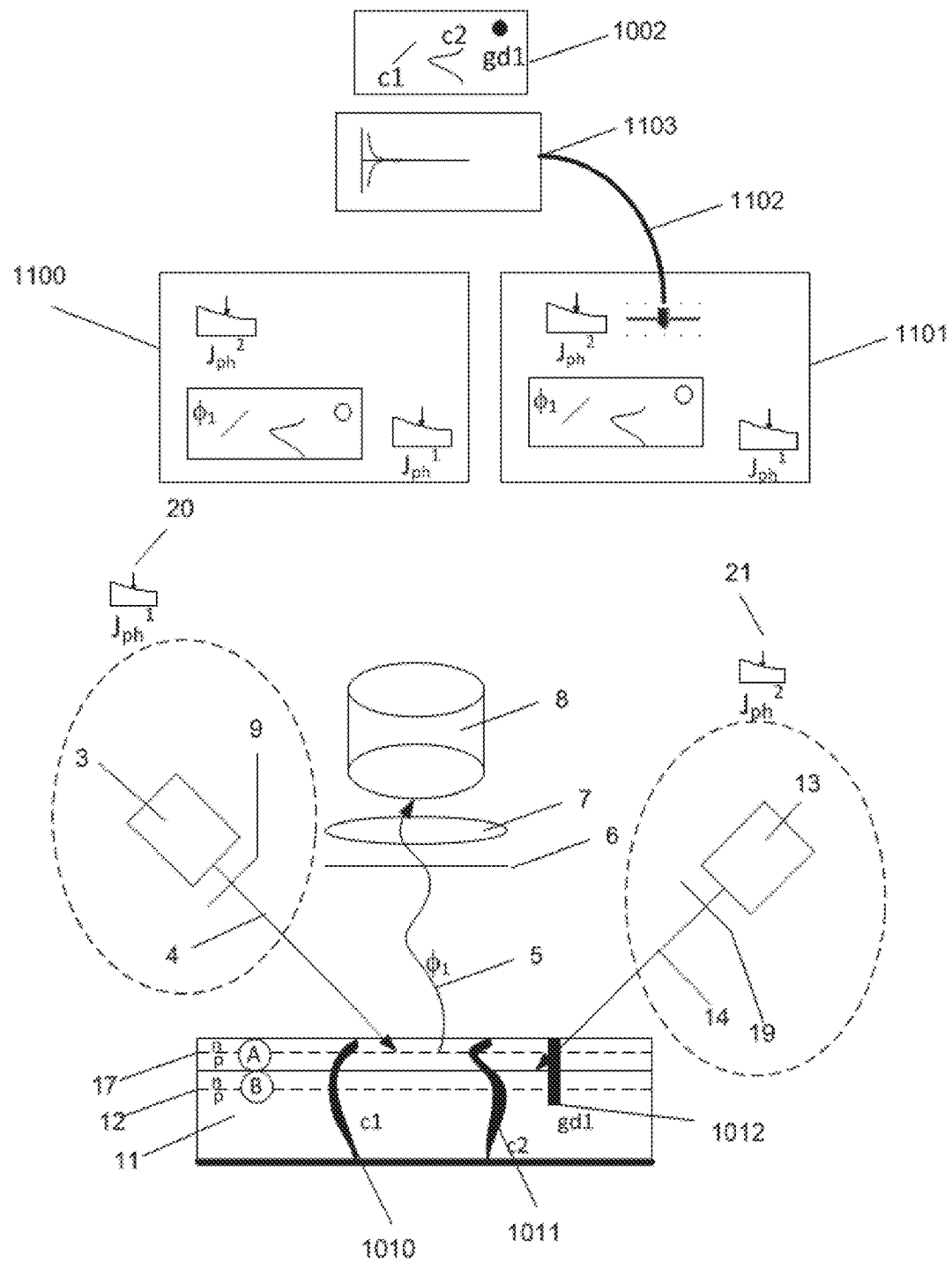
FIG. 15 shows a schematic representation of an apparatus for detecting a defect in a multi-junction solar cell that might be used for carrying out the method of FIG. 11.
Figure 16:
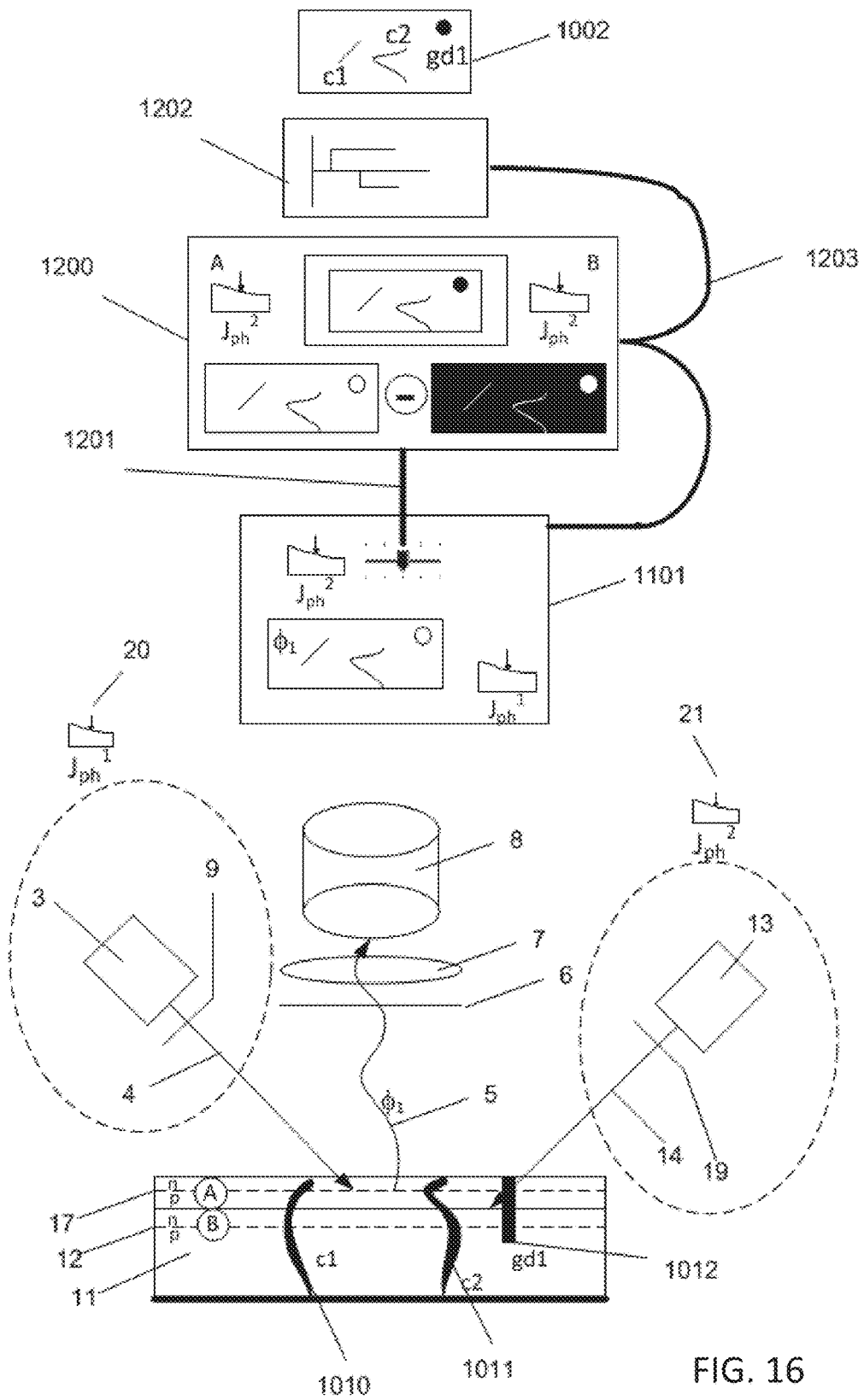
FIG. 16 shows a schematic representation of an apparatus for detecting a defect in a multi-junction solar cell that might be used for carrying out the method of FIG. 12.

FIGS. 14 to 16 each show a detailed implementation of an apparatus for detecting a defect in a multi-junction solar cell. For example, the apparatus of FIG. 14 is configured to carry out the method 700 of FIG. 10. The apparatus of FIG. 15 is configured to carry out the method 800 of FIG. 11. The apparatus of FIG. 16 is configured to carry out the method 900 of FIG. 12.

For the description in the following with regard to FIGS. 14 to 16, similar to FIG. 2, a solar cell 11 with two layers A 17, and B 12 is assumed. The apparatus can be easily extended to more than one junction. In this example, the cell exemplarily contains two mechanical cell defects c1 1010 and c2 1011, which penetrate the entire cell, as well as one growth defect gd1 1012. Similarly, in order to simplify the description, it is assumed that always junction A is imaged by the photoluminescence system, comprising a suitable filter 6 to isolate the photoluminescence emission 5 of junction A and to record it with the help of suitable optics 7 in combination with a detection system 8 spatially resolved. Also, this does not affect the general validity of the suggested apparatus, any other junction could be selected.

For the implementation of method 700, the apparatus, shown in FIG. 14, comprises one light source 3 with optional filter 9 to generate light 4 that is absorbed in junction A and to generate a certain photocurrent $J_{ph}^1$ 20 there. An image acquisition unit 1000 records the spatial distribution of the emitted photoluminescence for illumination conditions of layer 1 corresponding to a photocurrent of $J_{ph}^1$. An image processing unit 1001 analyzes the image for features creating an exponential decrease in contrast. A second processing unit 1002 evaluates the spatial distribution of the features identified in 1001 and attributes mechanical cell defects to essential 1-dimensional line features, whereas electrical growth defects are classified according to their rounded, 2-dimensional character.

In the above implementation, a first illumination unit (see FIG. 13) may comprise a light source 3 and a filter 9. A detecting unit may comprise a filter 6, a lens 7, and a detector 8 (detection system 8). Further, an image generating unit may comprise the image acquisition unit 1000.

FIG. 15 shows a second implementation of an apparatus for detecting a defect in a multi-junction solar cell. The setup of FIG. 15 contains a second light source 13 with optional filter 19. The wavelength distribution of its light 14 is such that it generates a photocurrent $J_{ph}^2$ 21 in a junction B. An image acquisition unit 1100 acquires an image of a layer A for one combined illumination condition, characterized by photocurrents $J_{ph}^1$ in the layer A and $J_{ph}^2$ in the layer B. Optionally the acquired image can then be passed on to image processing unit 1103, which analyzes the image for features creating an exponential increase or decrease in contrast, and/or to a second processing unit 1002 that evaluates the spatial distribution of the features identified in the image processing unit 1103 and attributes mechanical cell defects to essential 1-dimensional line features, whereas electrical growth defects are classified according to their rounded, 2-dimensional character.

In addition, the apparatus can be equipped with a feedback loop 1102 that enables the image processing unit 1103 to control the image acquisition unit 1101 such that $J_{ph}^2$ is adjusted by changing the illumination level of light source 13. In this feedback loop the image processing unit generates either a range of required photocurrent levels $J_{ph}^2$ for which images are acquired, or dynamically changes the $J_{ph}^2$ with a certain rate, while images are acquired continuously. In this operation mode the image processing unit 1103 identifies all pixels in the image that change with changing $J_{ph}^2$. These pixels are then plotted graphically and attributed to cell defects.

FIG. 16 shows a third implementation of an apparatus for detecting a defect in a multi-junction solar cell. There the basic photoluminescence setup with two light sources is unchanged. It also contains the image acquisition module 1101, which acquires a photoluminescence image for one $J_{ph}^1/J_{ph}^2$ combination. The acquisition module 1101 has a control input, where $J_{ph}^2$ can be set via an external control input. In addition, the apparatus contains an image calculation module 1200, which is capable of acquiring at least two images with the same $J_{ph}^1$, but different $J_{ph}^2$ settings. This module controls via the link 1201 the image acquisition module 1101.

The image calculation module subtracts two images with the same $J_{ph}^1$, but different $J_{ph}^2$. Optionally, the resulting image is passed on to the image processing unit 1202, which analyzes the image for features creating an abrupt change in contrast, and/or to a second processing unit 1002 that evaluates the spatial distribution of the features identified in the image calculation module 1200 or the image processing unit 1202 and attributes mechanical cell defects to essential 1-dimensional line features, whereas electrical growth defects are classified according to their rounded, 2-dimensional character. In addition, there is the option that the image processing unit 1202 also controls the current $J_{ph}^2$ for which images are acquired, either calculating a number of required $J_{ph}^2$ values or by dynamically changing $J_{ph}^2$ with a given rate. Via a control loop 1203 the image processing unit controls the units 1101 and 1200, such that images are acquired in the acquisition module 1101 for these $J_{ph}^2$ values and that the difference images are calculated in the image calculation module 1200. In this operation mode the image processing unit 1202 identifies all pixels in the difference images that change with changing $J_{ph}^2$. These pixels are then plotted graphically and attributed to cell defects.

In the above description and in the figures, the same reference numerals are used for corresponding features or units of different embodiments. However, the details expounded with regard to one of these features or units also hold accordingly for the features of other embodiments having the same reference sign. Further, the present invention is not limited to the concrete embodiments described above, which are merely examples how the present invention could be carried out. Other embodiments are possible, wherein it should be appreciated that features of one embodiment can be used in other embodiments as well.

In view of the above, aspects of the present disclosure are concerned with a method to detect defects, preferentially mechanical defects, in semiconductor components like solar cells comprising at least two p-n junctions stacked vertically on top of one another with the help of photoluminescence. In a first implementation only one junction is illuminated and the resulting photoluminescence image is analyzed for an exponential variation in contrast. In a modified approach, at least two adjacent junctions are illuminated and the illumination level of the junction not imaged is used to adjust the contrast of the defect in the junction imaged. Finally subtracting two photoluminescence images of one junction, acquired with the same illumination level of this junction, but with different illumination levels of at least one adjacent junction, increases the contrast of a defect significantly. This simplifies the manual or automatic detection.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for detecting a defect in a multi-junction solar cell comprising at least two vertically stacked p-n junctions, the method comprising:
    exciting a first p-n junction of the at least two vertically stacked p-n junctions by illuminating the solar cell with excitation light in a first excitation wavelength range at a first illumination intensity that is constant over time;

19 exciting a second p-n junction of the at least two vertically stacked p-n junctions by illuminating the solar cell with excitation light in a second excitation wavelength range at a second illumination intensity that changes over time;
detecting photoluminescence light emitted by photoluminescence of the first p-n junction; and
generating a plurality of spatially resolved photoluminescence image of the photoluminescence light emitted by the first p-n junction while the second illumination intensity is changed over time; and
observing the generated plurality of photoluminescence images for regions in which the intensity changes over time.

2. The method of claim 1, further comprising:
observing the first image for spatial intensity variations.

3. The method of claim 2, wherein
observing the first image for spatial intensity variations comprises observing the first image for exponential intensity variations.

4. A method for detecting a defect in a multi junction solar cell comprising at least two vertically stacked p-n junctions, the method comprising:
exciting a first p-n junction of the at least two vertically stacked p-n junctions by illuminating the solar cell with excitation light in a first excitation wavelength range;
exciting a second p-n junction of the at least two vertically stacked p-n junctions by illuminating the solar cell with excitation light in a second excitation wavelength range;
detecting photoluminescence light emitted by photoluminescence of the first p-n junction;
generating the a spatially resolved photoluminescence image of photoluminescence light emitted by photoluminescence of the first p-n junction under excitation of the first p-n junction at a first illumination intensity and under excitation of the second p-n junction at a second illumination intensity;
generating a second photoluminescence image of photoluminescence light emitted by photoluminescence of the first p-n junction under excitation of the first p-n junction at the first illumination intensity and under excitation of the second p-n junction at a third illumination intensity different from the second illumination intensity;
combining the first photoluminescence image and the second photoluminescence image to a third photoluminescence image by using a mathematical operation; and
observing the third photoluminescence image for spatial intensity variations.

5. The method of claim 4, wherein the mathematical operation is a subtraction of intensity values of one of the first and second photoluminescence image from the other of the first and second photoluminescence image.

6. The method of claim 1, wherein exciting the first p-n junction of the at least two vertically stacked p-n junctions by illuminating the solar cell with excitation light in a first excitation wavelength range is carried out at a first illumination intensity that is configured to create a photocurrent in the first p-n junction in a range of 1 to 100 mA/cm2.

7. The method of claim 6, wherein the photocurrent created in the first p-n junction is in a range of 10 to 20 mA/cm2.

8. The method of claim 1, wherein exciting the second p-n junction of the at least two vertically stacked p-n junctions by illuminating the solar cell with excitation light in a second excitation wavelength range is carried out at a

20 second illumination intensity that is configured to create a photocurrent in the second p-n junction in a range of 1 to 100 mA/cm2.

9. The method of claim 8, wherein the photocurrent created in the second p-n junction is in a range of 10 to 20 mA/cm2.

10. The method of claim 1, wherein
a center wavelength of the photoluminescence light emitted by photoluminescence of the first p-n junction is not included in the first excitation wavelength range.

11. The method of claim 1, wherein
a center wavelength of the photoluminescence light emitted by photoluminescence of the first p-n junction is not included in the first excitation wavelength range;
a center wavelength of the photoluminescence light emitted by photoluminescence of the first p-n junction is not included in the second excitation wavelength range; and
the first excitation wavelength range and the second excitation wavelength range do not overlap each other.

12. A computer program product stored on a computer-readable non-transitory storage device comprising program code portions for performing the steps of claim 1 when the computer program product is executed on a computing device.

13. An apparatus for detecting a defect in a multi-junction solar cell comprising at least two vertically stacked p-n junctions, the apparatus comprising:
a first illumination unit configured to excite a first p-n junction of the at least two vertically stacked p-n junctions by illuminating the solar cell with excitation light in a first excitation wavelength range at a first illumination intensity that is constant over time;
a second illumination unit configured to excite a second p-n junction of the at least two vertically stacked p-n junctions by illuminating the solar cell with excitation light in a second excitation wavelength range at a second illumination intensity that changes over time;
a detecting unit configured to detect photoluminescence light emitted by photoluminescence of the first p-n junction;
an image generating unit configured to generate a plurality of spatially resolved first photoluminescence image of the photoluminescence light emitted by the first p-n junction while the second illumination intensity is changed over time; and
an observation unit for observing the generated plurality of photoluminescence images for regions in which the intensity changes over time.

14. An apparatus for detecting a defect in a multi junction solar cell comprising at least two vertically stacked p-n junctions, the apparatus comprising:
a first illumination unit configured to excite a first p-n junction of the at least two vertically stacked p-n junctions by illuminating the solar cell with excitation light in a first excitation wavelength range;
a second illumination unit configured to excite a second p-n junction of the at least two vertically stacked p-n junctions by illuminating the solar cell with excitation light in a second excitation wavelength range;
a detecting unit configured to detect photoluminescence light emitted by photoluminescence of the first p-n junction; and
an image generating unit is configured to generate a spatially resolved first photoluminescence image of photoluminescence light emitted by photoluminescence of the first p-n junction under excitation of the first p-n junction at a first illumination intensity and under excitation of the second p-n junction at a second illumination intensity and to generate a second photoluminescence image of photoluminescence light emitted by photoluminescence of the first p-n junction under excitation of the first p-n junction at the first illumination intensity and under excitation of the second p-n junction at a third illumination intensity different from the second illumination intensity;

a combining unit configured to combine the first photoluminescence image and the second photoluminescence image to a third photoluminescence image by using a mathematical operation; and an observation unit configured to observe the third photoluminescence image for spatial intensity variations.

* * * * *